United States Patent
Kirby et al.

(10) Patent No.: US 11,116,748 B2
(45) Date of Patent: Sep. 14, 2021

(54) COMPOSITIONS AND METHODS FOR REDUCING WEIGHT GAIN

(71) Applicant: THE MEDICAL COLLEGE OF WISCONSIN, INC., Milwaukee, WI (US)

(72) Inventors: John Richard Kirby, Shorewood, WI (US); Orlando Grajo De Leon, Wauwatosa, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 163 days.

(21) Appl. No.: 16/511,630

(22) Filed: Jul. 15, 2019

(65) Prior Publication Data

US 2020/0016124 A1 Jan. 16, 2020

Related U.S. Application Data

(60) Provisional application No. 62/698,601, filed on Jul. 16, 2018.

(51) Int. Cl.
| | | |
|---|---|---|
| *A61K 31/4015* | (2006.01) | |
| *A61P 3/04* | (2006.01) | |
| *A61K 9/00* | (2006.01) | |
| *A61K 35/747* | (2015.01) | |

(52) U.S. Cl.
CPC ........ *A61K 31/4015* (2013.01); *A61K 9/0053* (2013.01); *A61K 35/747* (2013.01); *A61P 3/04* (2018.01)

(58) Field of Classification Search
CPC .............. A61K 2300/00; A61K 35/747; A61K 31/245; A61K 31/407; A61K 31/4164; A61K 31/43; A61K 31/454; A61K 31/496; A61K 31/505; A61K 31/519; A61K 31/5377; A61K 31/5383; A61K 31/545; A61K 31/546; A61K 31/551; A61K 31/5513; A61K 31/554; A61K 31/635; A61K 31/65; A61K 31/7036; A61K 31/7048; A61K 31/7052; A61K 31/7056; A61K 33/00; A61K 45/06; A61K 31/403; A61K 31/4015; A61K 31/609; A61K 31/612; A61K 9/0053; A61K 31/715; A61K 35/744; A61K 8/99; A61K 9/0058; A61K 9/0063; A61K 9/1664; A61K 9/5036; A61K 31/4045; A61K 31/4545; A61K 31/506; A61K 47/02; A61K 47/10; A61K 47/32; A61K 47/44; A61K 9/0014; A61K 9/0019; A61K 9/0048; A61K 9/06; A61K 9/10; A61K 9/1273; A61K 9/14; A61P 31/04; A61P 3/04; A61P 35/00; A61P 13/12; A61P 1/00; A61P 1/16; A61P 25/00; A61P 43/00; A61P 1/02; A61P 1/04; A61P 29/00; A61P 31/22; A61P 37/06; A61P 3/00; A61P 3/06; A61P 3/10; A61P 5/50; A61P 7/02; A61P 9/00; A61P 9/08; A61P 9/10; A61P 9/14; A61P 11/00; A61P 11/02; A61P 11/04; A61P 13/08; A61P 15/00; A61P 17/00; A61P 19/06; A61P 1/12; A61P 1/18; A61P 31/00; A61P 31/10; A61P 35/02; A61P 35/04; A23V 2002/00; A23V 2200/224; A23V 2200/3204; A23V 2200/3262; C12N 1/205; C12N 1/20; C12N 11/10; C12R 2001/225; A23L 33/135; A23C 2220/204; A23C 9/1234; A23Y 2220/71; A61Q 11/00; C07D 207/44; C07D 209/04; C07D 209/44; C07D 209/60; C07D 401/04; C07D 401/14; C12Q 1/02; Y02A 90/10; Y02A 50/30; A23K 10/18; A61L 15/36; A61L 15/46; A61L 2300/30; A61L 2300/404; A61L 2300/41; A61L 2300/428; A61L 2400/10; A61L 2400/12; A61L 29/005; A61L 29/085; A61L 29/16; A62C 2/06

See application file for complete search history.

(56) References Cited

U.S. PATENT DOCUMENTS 10,660,857 B2 * 5/2020 Prakash .................. A61P 9/08
2011/0217368 A1 9/2011 Prakash

FOREIGN PATENT DOCUMENTS

WO 2010124387 A1 * 11/2014 ............. A61K 35/74

OTHER PUBLICATIONS

Bahr, S. M., et al. "Risperidone-induced weight gain is mediated through shifts in the gut microbiome and suppression of energy expenditure." EBioMedicine 2.11 (2015): 1725-1734.
Center for Drug Evaluation and Research, Center for Biologics Evaluation and Research (2002), Estimating the safe starting dose in clinical trials for therapeutics in adult healthy volunteers, U.S. Food and Drug Administration, Rockville, Maryland, USA.
Ganzle, M.I G., et al. "Characterization of reutericyclin produced by Lactobacillus reuteri LTH2584." Appl. Environ. Microbiol. 66.10 (2000): 4325-4333.

(Continued)

*Primary Examiner* — Deborah K Ware
(74) *Attorney, Agent, or Firm* — Quarles & Brady LLP

(57) ABSTRACT

The present invention provides methods for using reutericyclin or an analog thereof to reduce weight gain or induce weight loss in a mammal. Also provided herein are methods for using reutericyclin-producing *Lactobacillus reuterii* bacteria as a probiotic to reduce weight gain or to induce weight loss, particularly for subjects receiving an antibiotic or xenobiotic treatment.

25 Claims, 8 Drawing Sheets
(7 of 8 Drawing Sheet(s) Filed in Color)

(56) References Cited

OTHER PUBLICATIONS

Hurdle, J. G., et al. "Evaluation of analogs of reutericyclin as prospective candidates for treatment of staphylococcal skin infections." Antimicrobial agents and chemotherapy 53.9 (2009): 4028-4031.

International Searching Authority, International Search Report and Written Opinion for application PCT/US2019/041803, dated Oct. 8, 2019.

Yendapally, R., et al. "N-substituted 3-acetyltetramic acid derivatives as antibacterial agents." Journal of medicinal chemistry 51.5 (2008): 1487-1491.

* cited by examiner

*Lactobacillus reuteri* deters weight gain during treatment with Risperidone by reducing visceral fat composition

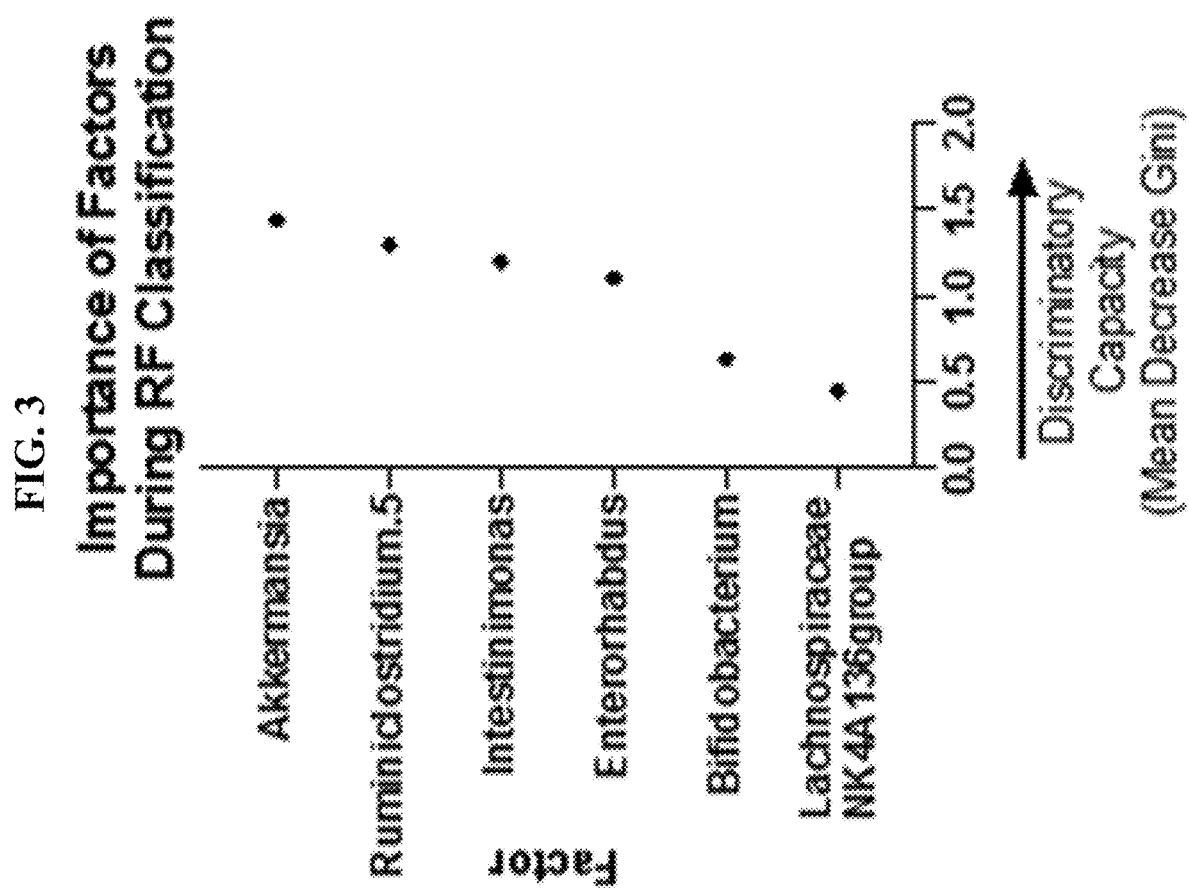

COMPOSITIONS AND METHODS FOR REDUCING WEIGHT GAIN

CROSS-REFERENCE TO RELATED APPLICATIONS

This patent application claims the benefit of priority of U.S. Provisional Patent Application No. 62/698,601, filed on Jul. 16, 2018, which is incorporated herein by reference in its entirety.

STATEMENT REGARDING FEDERALLY SPONSORED RESEARCH OR DEVELOPMENT

Not applicable.

BACKGROUND

Excessive weight gain associated with use of various medications including antibiotics and antipsychotic medications is a significant issue given its impact on general health. Unwanted weight gain and metabolic changes are some of the most common reasons for a patient's non-compliance with a treatment regimen, ultimately leading to the failure of the treatment. Accordingly, it would be desirable to identify and develop more effective compositions and methods to reduce or reverse weight gain associated with changes to the gut microbiome.

SUMMARY OF THE DISCLOSURE

In a first aspect, provided herein is a method of reducing weight gain or reversing weight gain in a human or another mammal. The method can comprise or consist essentially of administering a therapeutically effective amount of reutericyclin to reduce weight gain or induce weight loss using a clinically accepted administration route. The human or another mammal is being treated with an antibiotic or xenobiotic. The therapeutically effective amount of reutericyclin can be co-administered with an antibiotic or xenobiotic. The xenobiotic can be an antipsychotic medication. The antipsychotic medication can be selected from the group consisting of risperidone, clozapine, olanzapine, quetiapine, sertindole, and lithium. The antibiotic can be Amoxicillin, Ampicillin, Cefadroxil, Cephalexin, Clindamycin, Loracarbef, Metronidazole, Penicillin, Sulfisoxazole, Trimethroprim, Amoxicillin-Clavulanate, Ampicillin-Sulbactam Azithromycin, Cefoxitin, Ceftazidime, Ceftriaxone, Cefaclor, Cefdinir, Cefepime, Cefixime, Cefotaxime, Cefpodoxime, Cefprozil, Ceftibuten, Cefuroxime, Ciprofloxacin, Doxycycline, Gentamicin, Imipenem, Levofloxacin, Linezolid, Piperacillin-Tazobactam, Sulfamethoxazole-Trimethoprim, Tobramycin, Vancomycin. Macrolides: Azithromycin, Clarithromycin, Erythromycin, chlortetracycline, procaine, oxytetracycline, tylosin, bacitracin, neomycin sulfate, streptomycin, erythromycin, linomycin, oleandomycin, vancomycin, virginamycin, and bambermycin. The mode of administration can be oral.

In another aspect, provided herein is a method of reducing weight gain or reversing weight gain in a human or another mammal. The method can comprise or consist essentially of administering a therapeutically effective amount of reutericyclin-producing strain of *Lactobacillus reuterii* to reduce weight gain or induce weight loss using a clinically accepted administration route. The reutericyclin-producing strain can be *L. reuteri* LTH2584. The human or another mammal can be receiving treatment with an antibiotic or xenobiotic. The therapeutically effective amount of reutericyclin can be co-administered with an antibiotic or xenobiotic. The xenobiotic can be an antipsychotic medication. The antipsychotic medication can be selected from the group consisting of risperidone, clozapine, olanzapine, quetiapine, and sertindole. The antibiotic can be Amoxicillin, Ampicillin, Cefadroxil, Cephalexin, Clindamycin, Loracarbef, Metronidazole, Penicillin, Sulfisoxazole, Trimethroprim, Amoxicillin-Clavulanate, Ampicillin-Sulbactam Azithromycin, Cefoxitin, Ceftazidime, Ceftriaxone, Cefaclor, Cefdinir, Cefepime, Cefixime, Cefotaxime, Cefpodoxime, Cefprozil, Ceftibuten, Cefuroxime, Ciprofloxacin, Doxycycline, Gentamicin, Imipenem, Levofloxacin, Linezolid, Piperacillin-Tazobactam, Sulfamethoxazole-Trimethoprim, Tobramycin, Vancomycin. Macrolides: Azithromycin, Clarithromycin, Erythromycin, chlortetracycline, procaine, oxytetracycline, tylosin, bacitracin, neomycin sulfate, streptomycin, erythromycin, linomycin, oleandomycin, vancomycin, virginamycin, and bambermycin. The mode of administration can be oral.

In another aspect, provided herein is a pharmaceutical composition comprising *Lactobacillus reuterii* LTH2584 or a lysate thereof. The pharmaceutical composition can further comprise a probiotic bacterium of a strain other than *L. reuteri* LTH2584, or a lysate thereof, and pharmaceutically acceptable carrier. The *Lactobacillus reuterii* LTH2584 can be present in the composition at a quantity of at least 1,000,000 colony forming units per gram, based upon the total weight of the composition.

In a further aspect, provided herein is a lysate of *Lactobacillus reuterii* LTH2584.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or patent application file contains at least one drawing in color. Copies of this patent or patent application publication with color drawings will be provided by the Office upon request and payment of the necessary fee.

FIG. 3. Random Forest model classifies olanzapine-treated mice as well as risperidone based on changes in key taxa.

DETAILED DESCRIPTION OF THE DISCLOSURE

Figure 1:
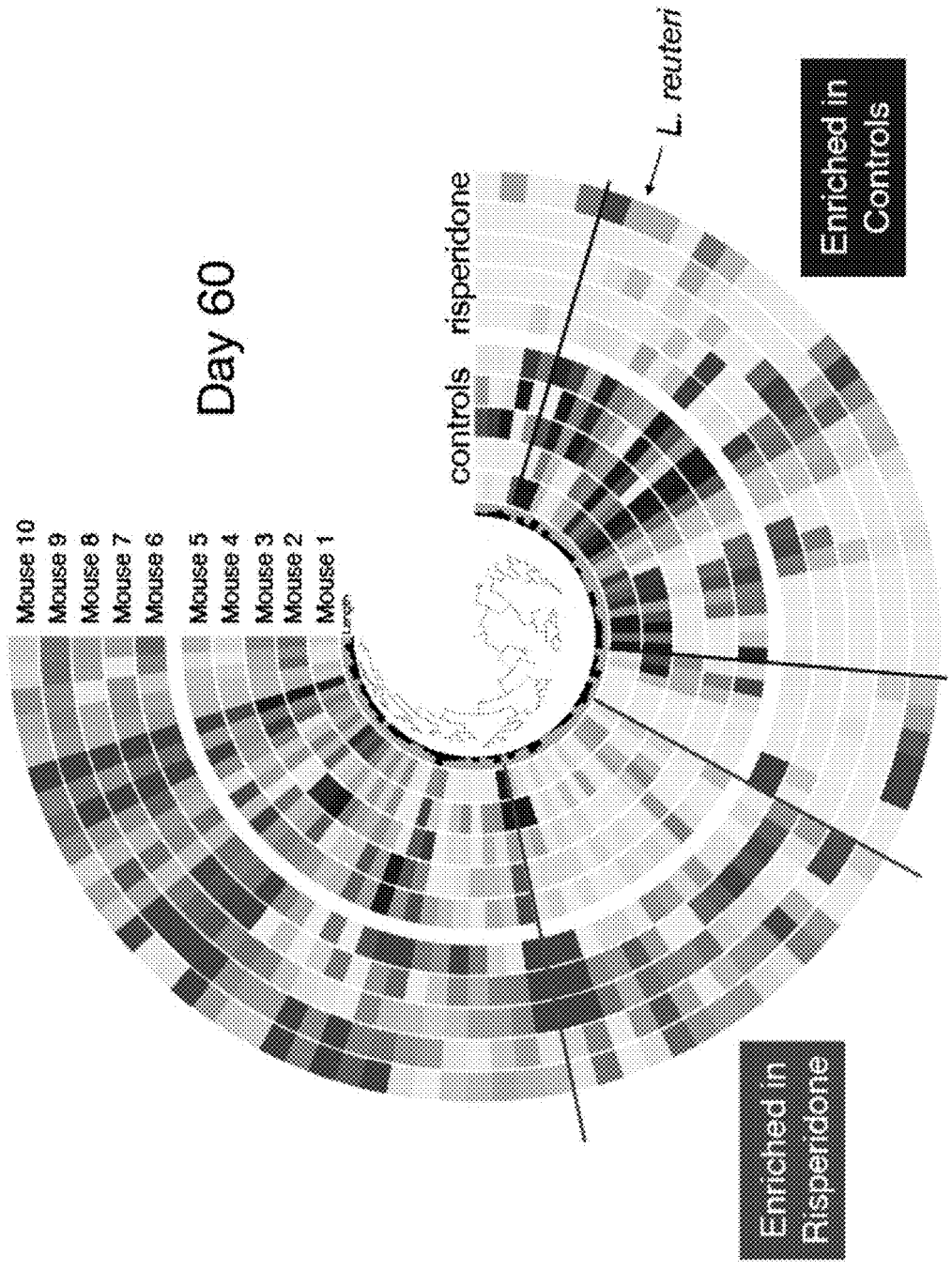
FIG. 1 demonstrates that *Lactobacillus reuterii* is selectively depleted in risperidone-treated mice. Shotgun metagenomic sequencing data (MiSeq, 2×250, high yield) from stool DNA was analyzed on the Anvi'o visualization platform. Bacterial genomes were refined to either genus or species level and ordered as slices within a ring by gene similarity (hierarchical clustering with a Hidden Markov Model). Metagenome groups enriched following risperidone treatment are indicated (red) relative to controls (blue).

The compositions and methods provided herein are based, at least in part, on the inventors' surprising discovery that reutericyclin, a small molecular weight antimicrobial produced by some strains of *Lactobacillus reuteri*. The present invention provides methods for using reutericyclin or an analog thereof to reduce weight gain or induce weight loss in a mammal. Also provided herein are methods for using reutericyclin-producing *Lactobacillus reuterii* bacteria as a probiotic to reduce weight gain or to induce weight loss, particularly for subjects receiving an antibiotic or xenobiotic treatment. Microbes that inhabit the human gastrointestinal (GI) tract are involved in xenobiotic processing, as evidenced by changes in metabolism in the absence of microbes (i.e., germ-free (GF) animals) or upon microbial perturbation (i.e., antibiotic treatment or dietary modulation). Without being bound to any particular theory or mechanism of action, it is believed that supplementation with reutericyclin, an analog thereof, or reutericyclin-producing *Lactobacillus reuterii* may induce and/or support beneficial weight loss, particularly in subject receiving treatment with an antibiotic or pharmaceutical that alters metabolism and is linked to weight gain or obesity.

Accordingly, in a first aspect, provided herein are methods of reducing or reversing weight gain or inducing weight loss in a subject. The methods comprise or consist essentially of the step of administering to a patient an amount of reutericyclin effective to inhibit or reverse weight gain. As used herein, the term "reutericyclin" refers to a highly hydrophobic, charged tetramic acid molecule produced by and isolated from particular strains of *Lactobacillus reuteri*. Referring to the main tautomeric form in solution, reutericyclin is (5R)-1-(2-decenoyl)-2-hydroxy-3-acetyl-5-isobutyl-Δ2-pyrroline-4-one, a N-acylated tetramic acid. N-alkyl reutericyclin analogs have been shown to retain activity against Gram-positive pathogens and other functional properties of reutericyclin. See, e.g., Yendapally et al., *J. Med. Chem.* 51, 1487-1491 (2008); Hurdle et al., *Antimicrob. Agents Chemother.* 53, 4028-4031 (2009).

In some cases, the method comprises administering a therapeutically effective amount of reutericyclin to reduce weight gain or induce weight loss using a clinically accepted administration route.

In some cases, the subject is being treated with an antibiotic or xenobiotic, including pharmaceuticals for which weight gain is a known side-effect. In some cases, reutericyclin can also be co-administered (e.g., sequentially or simultaneously) with or following administration of such an antibiotic or xenobiotic in order to preserve non-pathological intestinal bacterial flora in the subject to whom the reutericyclin is administered.

As used herein, the term "xenobiotic" refers to chemical compounds to which an organism (e.g., human, non-human mammal) is exposed that are extrinsic to the normal metabolism of that organism. The term encompasses synthetic drugs, small molecules, natural poisons, food additives, environmental pollutants, antibiotics, and other pharmaceuticals.

As used herein, the term "antibiotic" refers to a chemotherapeutic substance that is capable of killing and inhibiting growth of specific microorganisms, such as infectious bacteria and fungi. Antibiotics are classified based on their mechanism of action (i.e., if on the cell membrane, cell wall, or metabolism), chemical structure, spectrum of activity (i.e., if targeting gram-negative or gram-positive bacteria), or by mode of administration (e.g. oral, intravenous, or topical).

The term "reducing" refers to any indicia of success in the prevention or reduction of weight gain in a patient induced by or associated with an antibiotic or xenobiotic medication. The prevention or reduction of weight gain can be measured based on objective parameters, such as the results of a physical examination.

The term "reversing" refers to any indicia of success in causing the loss of antibiotic- or xenobiotic-associated weight gain established prior to the administration of reutericyclin or an analog thereof. The reduction of weight already gained can be measured based on objective parameters, such as the results of a physical examination.

Pharmaceuticals known to be associated with weight gain in patients receiving the medication include, without limitation antibiotics, antipsychotic medications (e.g., risperidone, haloperidol, olanzapine, clozapine, quetiapine, sertindole, and lithium), antidepressants (e.g., amitriptyline, paroxetine, and sertraline), oral corticosteroids, and drugs for treating diabetes and pre-diabetes (e.g., pre-diabetic states of impaired glucose tolerance) or its associated complications. In some cases, the methods and compositions provided herein are particularly advantageous to reduce weight gain or reverse weight gain in subjects to whom an antipsychotic medication such as risperidone or another atypical antipsychotic belonging to the chemical class of benzisoxazole derivatives. Risperidone has been shown to alter the gut microbiome and suppress non-aerobic resting metabolism in mice receiving the antipsychotic medication (Bahr et al., *E Bio Medicine* 2:1725-1734 (2015)). In particular, Bahr et al. demonstrated that risperidone treatment led to an overall reduction in observed taxa in the gut microbiome and selectively suppressed growth of organisms under anaerobic conditions. Other antipsychotics known to cause weight gain include, without limitation, quetiapine (Seroquel), paliperidone (invega), iloperidone (Fanapt), olanzapine (zyprexa), asenapine (saphris), lurasidone (latuda).

Antibiotics known to cause weight gain in farm animals and used in animal feed include, without limitation, chlortetracycline, procaine, penicillin, oxytetracycline, tylosin, bacitracin, neomycin sulfate, streptomycin, erythromycin, linomycin oleandomycin, virginamycin, and bambermycins.

Antibiotics known to induce weight gain in mice include, without limitation, chlortetracycline, penicillin, vancomycin, combinations of penicillin and vancomycin, streptomycin, and ciprofloxacin.

The following antibiotics (listed by category) are correlated with weight gain in humans. These associations have not been established via clinical trials, but are associated with either adult or pediatric exposure to antibiotics and the recipient's risk of developing obesity later in life. Taking any of the antibiotics listed either long term or single dose increases risk of developing obesity by 10-15%. Narrow-spectrum antibiotics: Amoxicillin, Ampicillin, Cefadroxil, Cephalexin, Clindamycin, Loracarbef, Metronidazole, Penicillin, Sulfisoxazole, Trimethroprim. Broad-spectrum antibiotics: Amoxicillin-Clavulanate, Ampicillin-Sulbactam Azithromycin, Cefoxitin, Ceftazidime, Ceftriaxone, Cefaclor, Cefdinir, Cefepime, Cefixime, Cefotaxime, Cefpodoxime, Cefprozil, Ceftibuten, Cefuroxime, Ciprofloxacin, Doxycycline, Gentamicin, Imipenem, Levofloxacin, Linezolid, Piperacillin-Tazobactam, Sulfamethoxazole-Trimethoprim, Tobramycin, Vancomycin. Macrolides: Azithromycin, Clarithromycin, Erythromycin.

As used herein, "obesity" means a medical condition in which excess body fat has accumulated to the extent that it may have a negative effect on health. One measurement of body fat is the body mass index (BMI), a measurement that compares weight and height, defines obesity as greater than 30 kg (weight) per $m^2$ (height$^2$). Obesity increases the likelihood of various diseases, particularly heart disease and type 2 diabetes (T2D).

The methods of this invention inhibit or reverse weight gain, including pharmaceutical-induced weight gain. The amount of reutericyclin or a reutericyclin analog adequate to accomplish this is defined as a "therapeutically effective amount." As used herein, a "therapeutically effective amount" means an amount of a compound or composition that, when administered to a subject for treating a disorder, condition, or disease, is sufficient to effect such treatment for the disorder, or condition, or disease. The "therapeutically effective amount" will vary depending on the compound or composition, the disorder, or condition, or disease state being treated, the severity or the disorder, or condition, or disease treated, the age and relative health of the subject, the route and form of administration, the judgment of the attending medical or veterinary practitioner, and other factors. The dosage schedule and amounts effective for this use, i.e., the "dosing regimen," will depend upon a variety of factors, including the type of the medication the patient is using, the amount of pharmaceutical-induced weight gain that has already occurred, the patient's physical status, the age and relative health of the subject, the route and form of administration, the judgment of the attending medical or veterinary practitioner, and other factors. In calculating the dosage regimen for a patient, the mode of administration also is taken into consideration.

In another aspect, provided herein is a probiotic composition including an appropriate quantity of reutericyclin-producing *Lactobacillus reuteri* bacteria, as well as methods for using the disclosed probiotic composition to induce and sustain weight loss in humans and non-human mammals, such as humans, horses, rats, mice, ruminants, primates, monkeys, hamsters, rabbits, and cats. As used herein, the term "probiotic" refers to a live or dead microbial food supplement which beneficially affects the animal, including human host by improving the individual's microbial balance in the gastrointestinal tract, e.g., *Lactobacillus reuteri* and other *Lactobacillus acidophilus*. That is, a probiotic microorganism is useful for changing the digestive system bacteria in animals when fed orally. For example, a probiotic microorganism, upon oral feeding, sustain or increase the population of appropriate *Bacteroides* bacteria in the gastrointestinal tract of the host. It is believed that successful establishment and propagation of appropriate reutericyclin-producing *Lactobacillus reuteri* bacteria in the gastrointestinal tract of a subject may induce and/or support beneficial weight loss, particularly in humans. The probiotic microorganism remains effective in the digestive system for substantial periods of time even after oral feeding is discontinued.

*Lactobacillus reuteri* is one of the few endogenous *Lactobacillus* species found in the gastrointestinal tract of vertebrates, including humans, rats, pigs and chickens. Reutericyclin-producing strains of *Lactobacillus reuteri* suitable for the compositions and methods provided herein include, without limitation, *Lactobacillus reuterii* LTH2584, *Lactobacillus reuterii* TMW1.106, *Lactobacillus reuterii* 1.112, and *Lactobacillus reuterii* 1.656. Each of these strains was isolated from the same industrial sourdough in 1988, 1994, and 1998, which has been maintained by continuous propagation. In preferred embodiments, the reutericyclin-producing bacteria are *L. reuteri* LTH2584.

Also provided herein are methods of administering a probiotic pharmaceutical composition comprising reutericyclin-producing *Lactobacillus reuteri* bacteria or a lysate thereof. In such cases, probiotic bacteria or their lysates according to the invention may be formulated as pharmaceutical compositions for clinical use and may comprise a pharmaceutically acceptable carrier, diluent or adjuvant. As used herein "lysates" refers to a sample of the probiotic bacterium which has been subject to lysis. A lysate may contain one or more soluble metabolites of the probiotic bacterium useful in the methods described herein. Lysis may occur by chemical or physical disruption, for example by addition of an osmotic agent or enzyme to the bacteria, or by the application of physical pressure, for example through sonic disruption. The lysate may be a mixture comprising the cellular contents of the probiotic bacterium. For example, one or more of fragments of cell wall or cell membrane, proteins, nucleic acids, carbohydrates, and organelles (disrupted or intact). The lysate may be suspended, for example in aqueous medium.

In some cases, reutericyclin-producing *Lactobacillus reuteri* bacteria are co-administered with or following administration of an antibiotic or xenobiotic to a subject in need thereof in order to preserve non-pathological intestinal bacterial flora in the subject to whom the reutericyclin-producing *L. reuteri* are administered.

In some cases, reutericyclin-producing *Lactobacillus reuteri* bacteria are provided as a probiotic in foods, medicines for humans and animals, and feedstock. Preferably, such probiotic reutericyclin-producing *Lactobacillus reuteri* bacteria are used alone, with an appropriate vehicle (carrier), or as an additive to a foodstuff or other composition suitable for human or animal (e.g., livestock, household pets) consumption. That is, the reutericyclin-producing *Lactobacillus reuteri* bacteria are useful because it can be added both to foodstuffs that do not contain probiotic bacteria (for the purpose of giving these products a probiotic value as well) and to foodstuffs already containing some probiotic bacteria (for the purpose of enhancing and/or completing their probiotic value). As used herein, livestock includes swine, cow, horse, goat, sheep, etc.; poultry includes fowls such as chicken, etc.; and pets include dogs, cats, etc.

For purposes of the present disclosure, the term "treating" or "treatment" describes the management and care of a patient for the purpose of combating the disease, condition, or disorder. The terms embrace both preventative, i.e., prophylactic, and palliative treatments. Treating includes the administration of a composition as described herein to prevent the onset of the symptoms or complications, alleviating the symptoms or complications, or eliminating the disease, condition, or disorder.

As used herein, "subject" refers to an animal or a patient for whom the described treatment is intended. For example, subjects treated according to the methods provided herein are mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans). a rodent (e.g., mouse, rat) or a primate (e.g., a monkey, baboon, human). In exemplary embodiments, the subject is a human. The term "subject" does not denote a particular age or sex. By "subject in need thereof," we mean an animal or human subject who has been diagnosed with a disease or condition requiring treatment.

Any appropriate route or mode of administration to the subject can be employed according to a method provided herein. In exemplary embodiments, reutericyclin or reutericyclin-producing bacteria are administered to a subject as a pharmaceutical composition and in an effective amount to treat and/or prevent a disorder (e.g., weight gain) as described herein. In some cases, the pharmaceutical composition comprises probiotic bacteria of the strain *Lactobacillus reuterii* LTH2584. In some cases, the probiotic bacteria may be provided in the form of a lysate. In some cases, a lysate of probiotic bacteria may be subjected to purification of filtration steps to remove other components, such as bacterial growth media or contaminants.

As used herein, the term "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism. As used herein, a "pharmaceutically acceptable carrier" refers to a carrier or diluent that does not cause significant irritation to an organism and does not abrogate the biological activity and properties of the administered compound. "Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Pharmaceutically active compositions and dosage forms of the disclosure include a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof. Additional examples of pharmaceutically acceptable salts and their methods of preparation and use are presented in *Handbook of Pharmaceutical Salts: Properties, and Use* (2002), which is incorporated herein by reference. In some cases, compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable carrier. The term "pharmaceutically acceptable carriers" as used herein refers to carriers, excipients, or stabilizers that are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

For probiotics, pharmaceutically acceptable carriers are particularly important to protect and preserve the probiotic bacteria until such time that the probiotic bacteria arrive within the gastrointestinal tract of a subject.

For determining a therapeutically effective dose, it can be advantageous to assess toxicity and therapeutic efficacy of a compound (e.g., reutericyclin or an analog thereof) in an in vitro assay (e.g., cell cultures) or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition provided herein can range from about 0.001 to 100 mg of an active ingredient per kg body weight of the subject (e.g., about 0.001 to 100 mg/kg body weight; about 0.1 to 40 mg/kg body weight; about 1 to 20 mg/kg body weight). In some cases, an appropriate dose of a pharmaceutical composition can be determined according to body surface area of a subject, calculated using the subject's height and weight, to whom the composition will be administered. In such cases, a dose can be provided as a particular amount of the composition per $m^2$ (e.g., $mg/m^2$). In other cases, dosages and dosage ranges appropriate for a composition provided herein can be determined using pharmacokinetic data (i.e., drug metabolism and clearance). As used herein, "pharmacokinetics" refers to the process by which a drug or pharmaceutical composition is absorbed, distributed, metabolized, and excreted from the body. Additional information about dosage calculation can be found in Center for Drug Evaluation and Research, Center for Biologics Evaluation and Research (2002), *Estimating the safe starting dose in clinical trials for therapeutics in adult healthy volunteers*, U.S. Food and Drug Administration, Rockville, Md., USA.

As stated above, a therapeutically effective dose level will depend on many factors. In addition, it is well within the skill of the art to start doses of the active composition at relatively low levels, and increase the dosage until the desired effect is achieved. Efficacy of the methods provided herein can be determined using any appropriate method. For example, weight gain may be determined and evaluated with any one of several objective, standard instruments known in the art, which include scales and instruments that measure body fat percentage. The simple instrument of a scale is routinely used by all professional health care practitioners. More sophisticated instruments to measure body fat percentage operate based on skin-fold methodology and measurement of body density or electrical resistance.

A formulation may contain a single (unit) dose of probiotic bacteria, or lysate thereof. Suitable doses of probiotic bacteria (intact or lysed) may be in the range $10^4$ to $10^{12}$ colony forming units (cfu), e.g. one of $10^4$ to $10^{10}$, $10^4$ to $10^8$, $10^6$ to $10^{12}$, $10^6$ to $10^{10}$, or $10^6$ to $10^8$ cfu. In some embodiments doses may be administered once or twice daily.

Pharmaceutical unit dosage forms of the compounds of this disclosure are suitable for oral, mucosal (e.g., nasal, sublingual, vaginal, buccal, or rectal), parenteral (e.g., bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Clinicians, physicians, and other health care professionals can administer a composition to a subject in need thereof according to a method provided herein. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as administration of a composition provided herein is tolerated by the subject.

It is to be understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

In the specification and in the claims, the terms "including" and "comprising" are open-ended terms and should be interpreted to mean "including, but not limited to . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

The terms "including", "such as", "for example" and the like are intended to refer to exemplary embodiments and not to limit the scope of the present disclosure.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1—Effects of Risperidone Treatment on Weight Gain

To determine whether *Lactobacillus reuterii* is selectively depleted in risperidone-treated mice, C57bl/6J female mice were treated with risperidone for 60 days. Shotgun metagenomic sequencing data (MiSeq, 2×250, high yield) from stool DNA were analyzed on the Anvi'o visualization platform. Bacterial genomes were refined to either genus or species level and ordered as slices within a ring by gene similarity (hierarchical clustering with a Hidden Markov Model). In FIG. 1, metagenomes of risperidone treated mice are colored red and control mice colored blue. As shown in FIG. 1, C57bl/6J female mice treated with risperidone for 60 days displayed statistically significant weight gain and had statistically significant differences in their bacterial composition. Transfer of fecal or viral fractions from drug treated mice was sufficient to produce enhanced weight gain relative to controls.

Figure 2A:
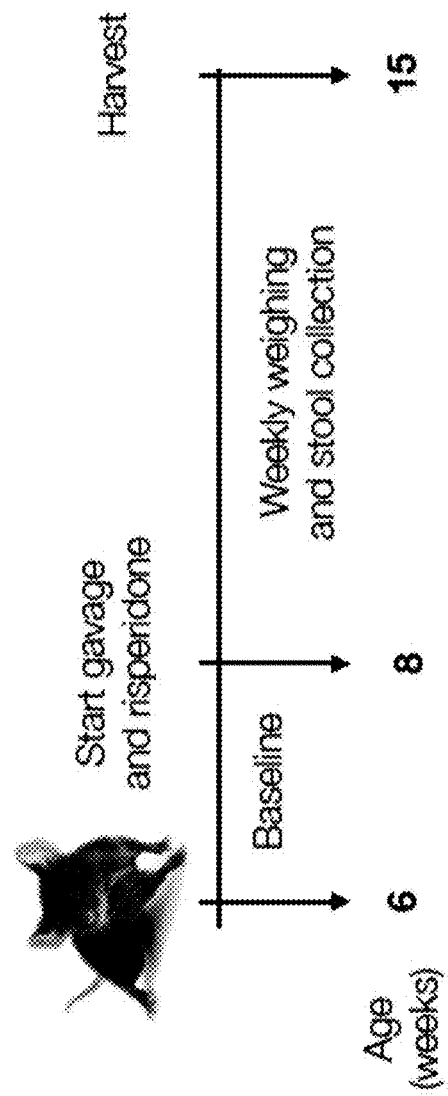
FIGS. 2A-2C show that supplementation with reutericyclin-producing strain LTH2584 abrogates weight gain in mice. (A) Experimental design: C57Bl/6J female mice arrived at 6 weeks of age and were allowed to acclimate to the facility for two weeks (n=10/group). Baseline stool was collected every other day through 15 weeks where visceral fat tissue was harvested. (B) Shown are body mass increases for control animals (blue), those receiving *L. reuteri* producing reutericyclin (green), or *L. reuteri* producing reutericyclin+risperidone (magenta), or *L. reuteri* unable to produce reutericyclin+risperidone (red). (C) Visceral fat pads were dissected at day 64 from each mouse, weighed, and quantified. Color coding is the same as above in FIG. 2B. Fat pads from risperidone-treated mice that also received *L. reuteri* capable of producing reutericyclin were significantly reduced relative to those animals that received risperidone treatment alone (Wilcoxon, *p<0.05).
Figure 2B:
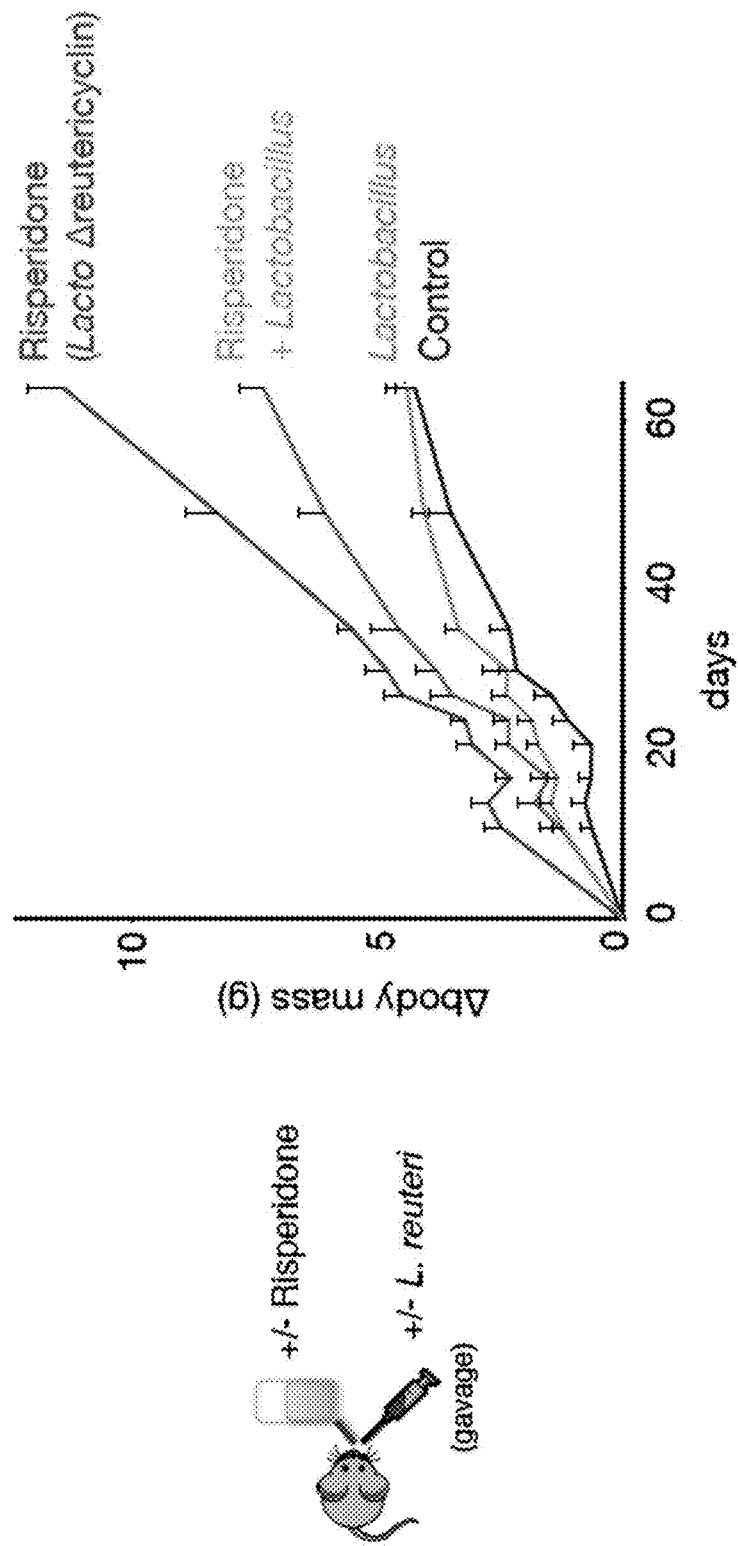

To further investigate the effects of risperidone treatment on weight gain, female mice were treated with *L. reuteri* producing reutericyclin, with or without risperidone treatment. C57Bl/6J female mice arrived at 6 weeks of age and were allowed to acclimate to the facility for two weeks (n=10/group) (FIG. 2A). 8-week old C57Bl/6J female mice were treated daily via gavage with 100 µL containing either $3\times10^8$ CFUs of *Lactobacillus reuterii* strain LTH2584 (a reutericyclin-producing strain) or buffer (phosphate buffered saline). Drinking water was supplemented with buffer or risperidone (20 mg/mL). Baseline stool was collected every other day through 15 weeks where visceral fat tissue was harvested. FIG. 2B shows body mass increases for control animals (green), those receiving *L. reuteri* producing reutericyclin (blue), or *L. reuteri* producing reutericyclin+risperidone (magenta), or *L. reuteri* unable to produce reutericyclin+risperidone (red). Animals receiving risperidone only were nearly identical to the red line (data not shown). Weight gain in mice treated with risperidone plus *L. reuteri* producing reutericyclin (magenta) is abrogated at 64 days of treatment relative to those animals receiving risperidone plus *L. reuteri* lacking the capability to produce reutericyclin (red) as determined by Wilcoxon (*p<0.05), yet showed some weight gain relative to control animals (green) or bacteria-only treated mice (blue).

Figure 2C:
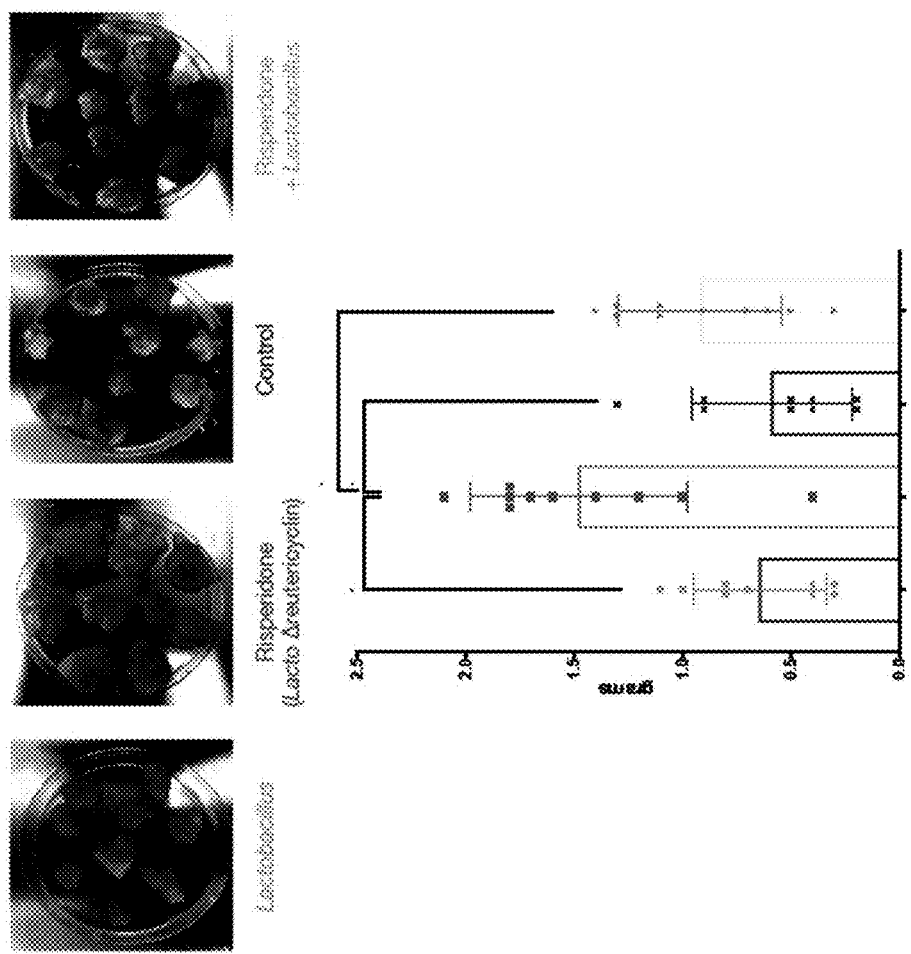

Visceral fat pads were dissected at day 64 from each mouse, weighed, and quantified. As shown in FIG. 2C, fat pads from risperidone treated mice that also received *L. reuteri* capable of producing reutericyclin were significantly reduced relative to those animals that received risperidone treatment alone (Wilcoxon, *p<0.05).

Discussion

This example demonstrates that treatment with reutericyclin prevents weight gain associated with risperidone treatment. These data suggest that reutericyclin can be developed as a weight loss agent or to prevent or abrogate weight gain associated with some pharmaceutical treatments.

Example 2—Random Forest and Linear Models can Predict Weight Gain from Antipsychotics A set of taxonomic changes that characterize the microbiomes of risperidone-treated animals and reutericyclin-treated animals was identified. Using a machine learning method known as Random Forest (RF), these differences were used to generate a prediction model. The minimal components of the model and their relative importance are shown in FIG. 3. This model can also be applied to predict weight gain from other drugs in the second-generation anti-psychotic class, including olanzapine treated animals (AUC=0.95). This result indicates that 1) obesity-causing microbiome changes due to risperidone treatment are also observed to occur in response to other anti-psychotics and 2) either reutericyclin or reutericyclin-producing probiotics (*L. reuterii* strain LTH2584) may be used to treat obesity from other anti-psychotics.

Figure 4:
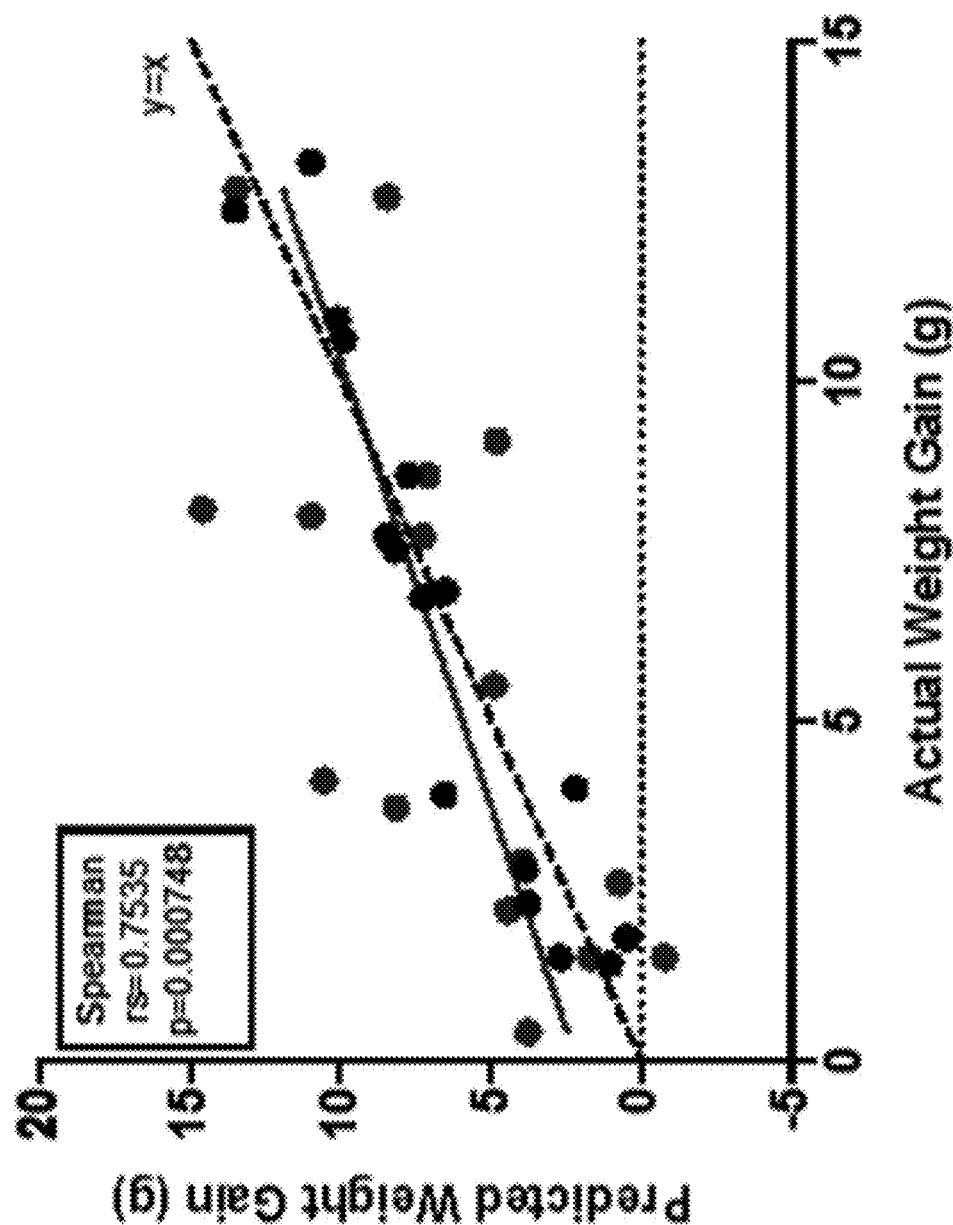
FIG. 4. Linear model (LM) predictions against the actual weight gained for risperidone, reutericyclin, and probiotic treated mice. The randomized training set animals are shown in black and the test set animals are shown in blue. A line of best fit (solid blue line) and the y=x line (black, dashed line) are there for reference. A Spearman rank-order correlation was performed to determine significance of the predicted weights (p=0.000748).
Figure 5:
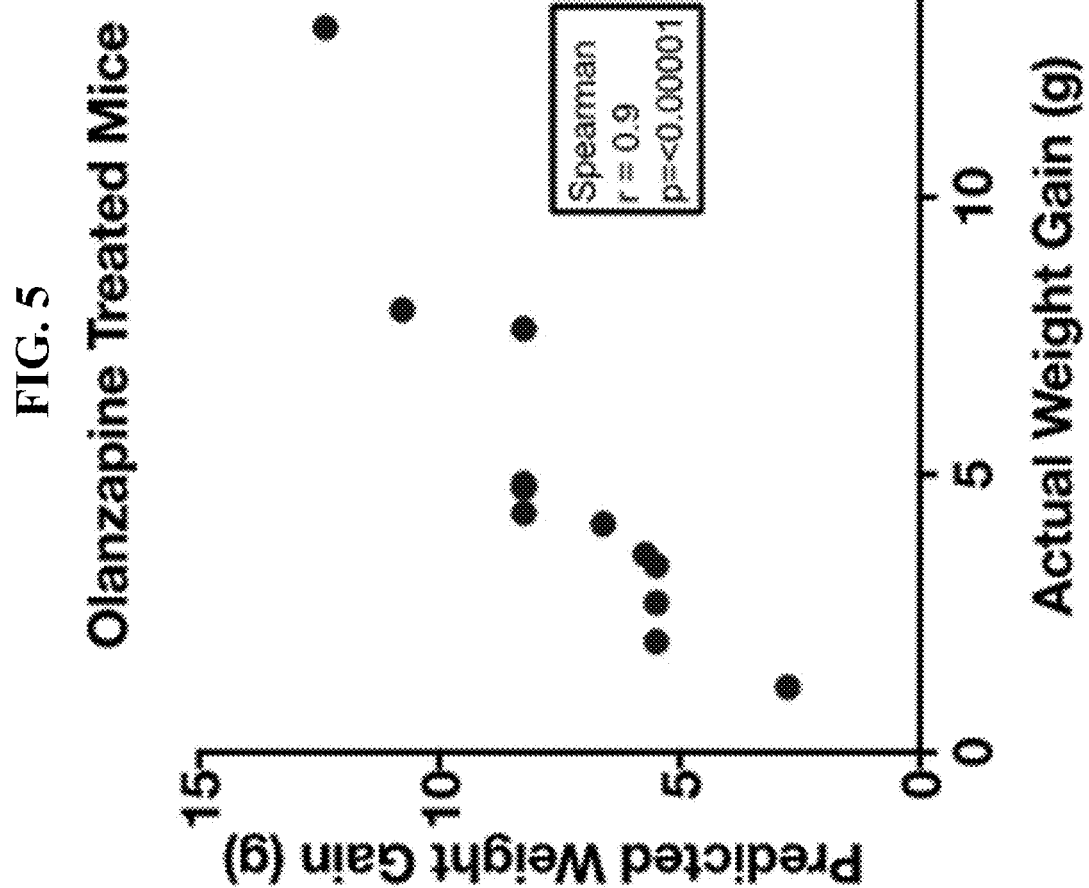
FIG. 5. Linear model (LM) predicts the weight gain in olanzapine-treated animals (p<0.00001).

Using the observed changes above, we generated a linear model to predict the weight gain for risperidone treated animals. It was determined that this linear model predicts the weight gain associated with risperidone use, reutericyclin treatment and probiotic strain LTH2584 treatment (FIG. 4, Spearman Rank Order Correlation, p=0.000748). The training and test sets were randomized and separated before performing the model construction and model evaluation. The model was tested on olanzapine-treated animals and it was determined that the model performs equally well to predict the weight gain associated with another anti-psychotic (FIG. 5 Spearman Rank Order Correlation, p<0.00001). The taxa identified to be important in characterizing body weight changes associated with risperidone, reutericyclin treatment, and olanzapine treatment can be adapted to a PCR-based diagnostic to predict treatment response and weight gain.

Figure 6:
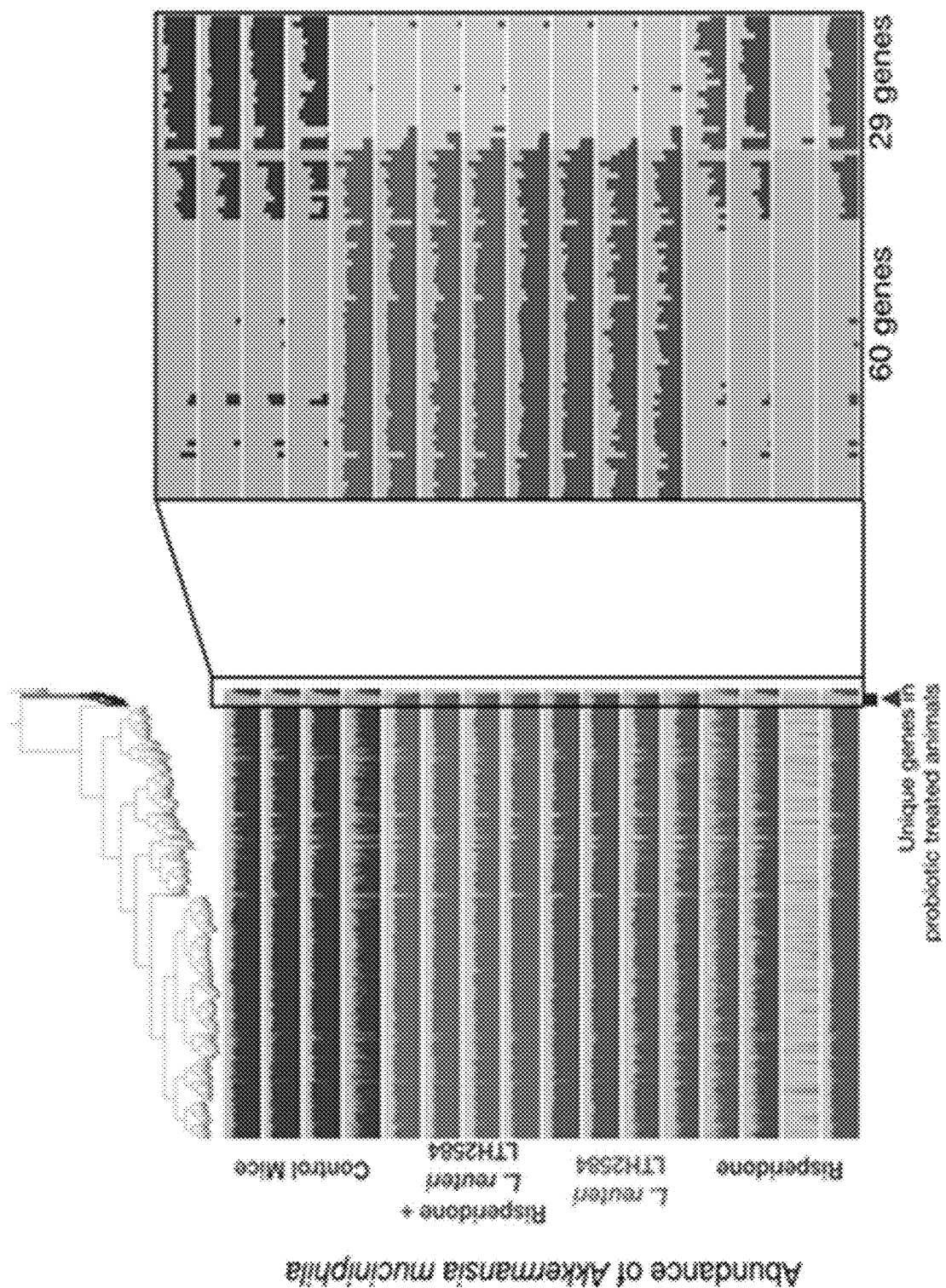
FIG. 6. Detection of unique genes in *Akkermansia muciniphila* found in probiotic-treated animals can be adapted to a PCR-based test for treatment efficacy.

To increase predictive specificity, we can generate a classifier for treatment response and a linear model of weight gain in response to these treatments (risperidone and reutericyclin) based on gene-specific differences. For example, *Akkermansia muciniphila* strains have unique 26.1 kb genomic signature in risperidone-treated animals compared to probiotic LTH2584 treated animals. In contrast, *Akkermansia muciniphila* has a unique 37.8 kb stretch (FIG. 6) in LTH2584 probiotic treated animals. A PCR-based test can be generated to identify these genes in order to determine treatment efficacy.

Lastly, 20 gene reutericyclin synthesis-like gene clusters (blastp, e-value=<0.0005) were identified in human datasets (stool) that were differentially abundant in healthy human controls (n=50) relative to pre-diabetic patients (n=40) that reported weight gain at time of sampling. These genes, as well as other specific gene trends, can be incorporated into a random forest and linear model to predict weight gain in humans. These data suggest that reutericyclin-like molecules may have a role in human weight gain.

The present invention is not intended to be limited to the foregoing examples, but encompasses all such modifications and variations as come within the scope of the appended claims.

We claim:

1. A method of reducing weight gain or reversing weight gain in a human or another mammal, the method comprising administering a therapeutically effective amount of reutericyclin to reduce weight gain or induce weight loss using a clinically accepted administration route.

2. The method of claim 1, wherein the human or another mammal is being treated with an antibiotic or xenobiotic.

3. The method of claim 1, wherein the therapeutically effective amount of reutericyclin is co-administered with an antibiotic or xenobiotic.

4. The method of claim 2, wherein the xenobiotic is an antipsychotic medication.

5. The method of claim 4, wherein the antipsychotic medication is selected from the group consisting of risperidone, clozapine, olanzapine, quetiapine, sertindole, and lithium.

6. The method of claim 2, wherein the antibiotic is selected from Amoxicillin, Ampicillin, Cefadroxil, Cephalexin, Clindamycin, Loracarbef, Metronidazole, Penicillin, Sulfisoxazole, Trimethroprim, Amoxicillin-Clavulanate, Ampicillin-Sulbactam Azithromycin, Cefoxitin, Ceftazidime, Ceftriaxone, Cefaclor, Cefdinir, Cefepime, Cefixime, Cefotaxime, Cefpodoxime, Cefprozil, Ceftibuten, Cefuroxime, Ciprofloxacin, Doxycycline, Gentamicin, Imipenem, Levofloxacin, Linezolid, Piperacillin-Tazobactam, Sulfamethoxazole-Trimethoprim, Tobramycin, Vancomycin, Macrolides: Azithromycin, Clarithromycin, Erythromycin, chlortetracycline, procaine, oxytetracycline, tylosin, bacitracin, neomycin sulfate, streptomycin, erythromycin, linomycin, oleandomycin, vancomycin, virginamycin, and bambermycin.

7. The method of claim 1, wherein the mode of administration is oral.

8. The method of claim 1, wherein the human or another mammal is being treated with an antipsychotic medication.

9. The method of claim 8, wherein the therapeutically effective amount of reutericyclin is co-administered with the antipsychotic medication.

10. The method of claim 8, wherein the antipsychotic medication is an atypical antipsychotic medication.

11. The method of claim 10, wherein the atypical antipsychotic medication is selected from risperidone, clozapine, olanzapine, quetiapine and sertindole.

12. The method of claim 10, wherein the atypical antipsychotic medication is olanzapine.

13. The method of claim 8, wherein the antipsychotic medication is a benzisoxazole antipsychotic medication.

14. The method of claim 13, wherein the benzisoxazole antipsychotic medication is risperidone.

15. The method of claim 13, wherein the therapeutically effective amount of reutericyclin is co-administered with the benzisoxazole antipsychotic medication.

16. The method of claim 1, wherein the method comprises orally administering a pharmaceutical composition comprising an antipsychotic medication and the therapeutically effective amount of reutericyclin.

17. The method of claim 1, wherein the method comprises orally administering a pharmaceutical composition comprising a benzisoxazole antipsychotic medication and the therapeutically effective amount of reutericyclin.

18. The method of claim 1, wherein the method comprises orally administering a pharmaceutical composition comprising an antipsychotic medication and the therapeutically effective amount of reutericyclin.

19. The method of claim 1, wherein the method comprises orally administering a pharmaceutical composition comprising a benzisoxazole antipsychotic medication and the therapeutically effective amount of reutericyclin.

20. A method of reducing visceral fat in a human or another mammal being treated with an antipsychotic medication, the method comprising administering a therapeutically effective amount of reutericyclin.

21. The method of claim 20, wherein the method comprises orally administering a pharmaceutical composition comprising the antipsychotic medication and the therapeutically effective amount of reutericyclin.

22. The method of claim 20, wherein the method comprises administering a pharmaceutical composition comprising an atypical antipsychotic medication and the therapeutically effective amount of reutericyclin.

23. The method of claim 22, wherein the atypical antipsychotic medication is olanzapine.

24. The method of claim 20, wherein the method comprises administering a pharmaceutical composition comprising a benzisoxazole antipsychotic medication and the therapeutically effective amount of reutericyclin.

25. The method of claim 24, wherein the benzisoxazole antipsychotic medication is risperidone.

* * * * *